(12) United States Patent
Choi et al.

(10) Patent No.: US 8,656,794 B2
(45) Date of Patent: Feb. 25, 2014

(54) APPARATUS FOR DISSOLUTION EXPERIMENT OF MINERAL

(75) Inventors: Jung-Hae Choi, Daejeon (KR);
Byung-Gon Chae, Daejeon (KR);
Yong-Je Kim, Daejeon (KR)

(73) Assignee: Korea Institute of Geoscience and Mineral Resources (KIGAM), Daejeon (KR)

( * ) Notice: Subject to any disclaimer, the term of this patent is extended or adjusted under 35 U.S.C. 154(b) by 67 days.

(21) Appl. No.: 13/526,886

(22) Filed: Jun. 19, 2012

(65) Prior Publication Data

US 2013/0098177 A1    Apr. 25, 2013

(30) Foreign Application Priority Data

Oct. 21, 2011    (KR) .................. 10-2011-0108059

(51) Int. Cl.
*G01N 33/00*        (2006.01)
(52) U.S. Cl.
USPC ........................................... 73/866; 73/865.8
(58) Field of Classification Search
USPC ............................ 73/866, 865.8; 422/264, 266
See application file for complete search history.

(56) References Cited

U.S. PATENT DOCUMENTS

| | | | | |
|---|---|---|---|---|
| 3,618,395 A | * | 11/1971 | Melliger, M.W. ............... | 73/866 |
| 4,593,563 A | * | 6/1986 | Laine et al. ................... | 73/865.8 |
| 4,754,657 A | * | 7/1988 | Schneider ...................... | 73/866 |
| 5,076,107 A | * | 12/1991 | Timmermans et al. ......... | 73/866 |
| 5,827,984 A | * | 10/1998 | Sinnreich et al. .............. | 73/866 |
| 6,484,595 B1 | * | 11/2002 | Kramer ........................... | 73/866 |
| 6,497,157 B1 | * | 12/2002 | Viegas et al. .................. | 73/866 |
| 8,281,675 B2 | * | 10/2012 | Levin et al. .................... | 73/866 |
| 8,505,398 B2 | * | 8/2013 | Yang et al. ..................... | 73/866 |

FOREIGN PATENT DOCUMENTS

| | | |
|---|---|---|
| JP | 2003-057229 A | 2/2003 |
| JP | 2003-057361 A | 2/2003 |
| JP | 2005-069949 A | 3/2005 |

\* cited by examiner

*Primary Examiner* — Leonard Chang
*Assistant Examiner* — Natalie Huls
(74) *Attorney, Agent, or Firm* — Ladas & Parry LLP

(57) ABSTRACT

An apparatus for dissolution experiment of mineral is disclosed. The apparatus for a dissolution experiment of mineral according to the inventive concept includes a main body including frames, a mounting unit including a container whose mouth is open so as to contain an alkaline solution, a first mineral sample and a second mineral sample contacting with each other in the alkaline solution, a cylinder including a plunger that is attached to the main body and movable so as to be inserted in and separated from the container for pressing the first mineral sample toward the second mineral sample included in the container, and a load cell supporting the mounting unit from the below and measuring a pressure applied to the second mineral sample.

10 Claims, 3 Drawing Sheets

APPARATUS FOR DISSOLUTION EXPERIMENT OF MINERAL

CROSS-REFERENCE TO RELATED APPLICATIONS

This application claims priority under 35 U.S.C. §119 to Korean Patent Application No. 10-2011-000108059, filed on Oct. 21, 2011, in the Korean Intellectual Property Office, the entire contents of which are incorporated herein by reference.

BACKGROUND

Example embodiments of inventive concepts relates to an experiment apparatus for measuring long-term change of mineral, and more particularly, to an experiment apparatus capable of measuring dissolution behavior of mineral under the condition of various pressures, temperatures, and pHs.

In a facility for burying high level radioactive waste, a covering material such as bentonite or cement is used so that the waste may not be discharged from the facility. Bentonite is a clay mineral including quartz and may prevent the waste from contacting with water by expending itself when reacts to water such as underground water.

Like the above, high level radioactive waste is buried in a depth about 1 km under the ground, and a covering material such as bentonite is used for isolating the waste from surroundings. It is important to consider that the covering material may change, especially, dissolve, when the covering material is maintained in the underground condition of high temperature, high pressure, and high pH.

Accordingly, it is possible to bury high level radioactive waste safely, only when dissolution behavior of mineral such as quartz under the various underground condition may be figured out exactly. However, as development of the apparatus for experimenting dissolution behavior of mineral has not been achieved in the middle of reproducing the underground condition, there have been problems that dissolution behavior of mineral may not be easily figured out quantitatively.

SUMMARY

The inventive concept aims to provide an apparatus for dissolution experiment of mineral that is capable of reproducing various condition of the underground depth, thereby measuring long-term dissolution behavior of mineral in the underground condition accurately.

According to an example embodiment, there is provided an apparatus for dissolution experiment of mineral including a main body including a frame, a mounting unit including a container whose mouth is open so as to contain an alkaline solution, a first mineral sample and a second mineral sample that are contacting with each other in the alkaline solution, a cylinder including a plunger that is movable so as to be inserted into and separated from the container, and a load cell supporting the mounting unit from the bottom and measuring a pressure applied to the second mineral sample.

According to an example embodiment, the apparatus further includes a temperature controller for controlling the temperature of the first mineral sample and the second mineral sample in the mounting unit, wherein the temperature controller is a heat wire pad that is installed so as to wrap exterior surface of the mounting unit and includes heat wires generating heat inside by electric resistance.

The plunger further includes a regulator for maintaining a pressure applied to the first mineral sample constantly.

Also, the apparatus further includes a displacement sensor for measuring shift distance of the plunger, wherein the displacement sensor includes a sensor that is installed so as to be fixed to the main body and a mover that shifts along with the plunger combined thereto and whose ending portion is disposed on a sensing path of the sensor. The displacement sensor senses the distance from the sensor to the mover, and measures a displacement variation of the plunger.

Meanwhile, the mounting unit is formed in a tube shape with closed bottom, and the second mineral sample is inserted into the mounting unit, but the first mineral sample is formed in a sharp wedge shape while being inserted into the mounting unit, such that the lower end surface of the wedge part contacts with the upper end surface of the second mineral sample, and the alkaline solution is contained between the wedge part of the first mineral sample and the second mineral sample. The area where the first mineral sample contacts with the second mineral sample is desired be 1~3 mm in diameter.

Also, the mounting unit includes a cylindrical tube, a supporter inserted into the lower portion of the tube and supporting the second mineral sample, and an O-ring interposed between the exterior surface of the supporter and the inner surface of the tube and preventing the alkaline solution from being leaked out. And the tube of the mounting unit is composed of polycarbonate.

A concave groove is formed on the bottom of the supporter such that a protrusion formed on the upper surface of the load cell may be inserted.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF THE EMBODIMENTS

Figure 1:
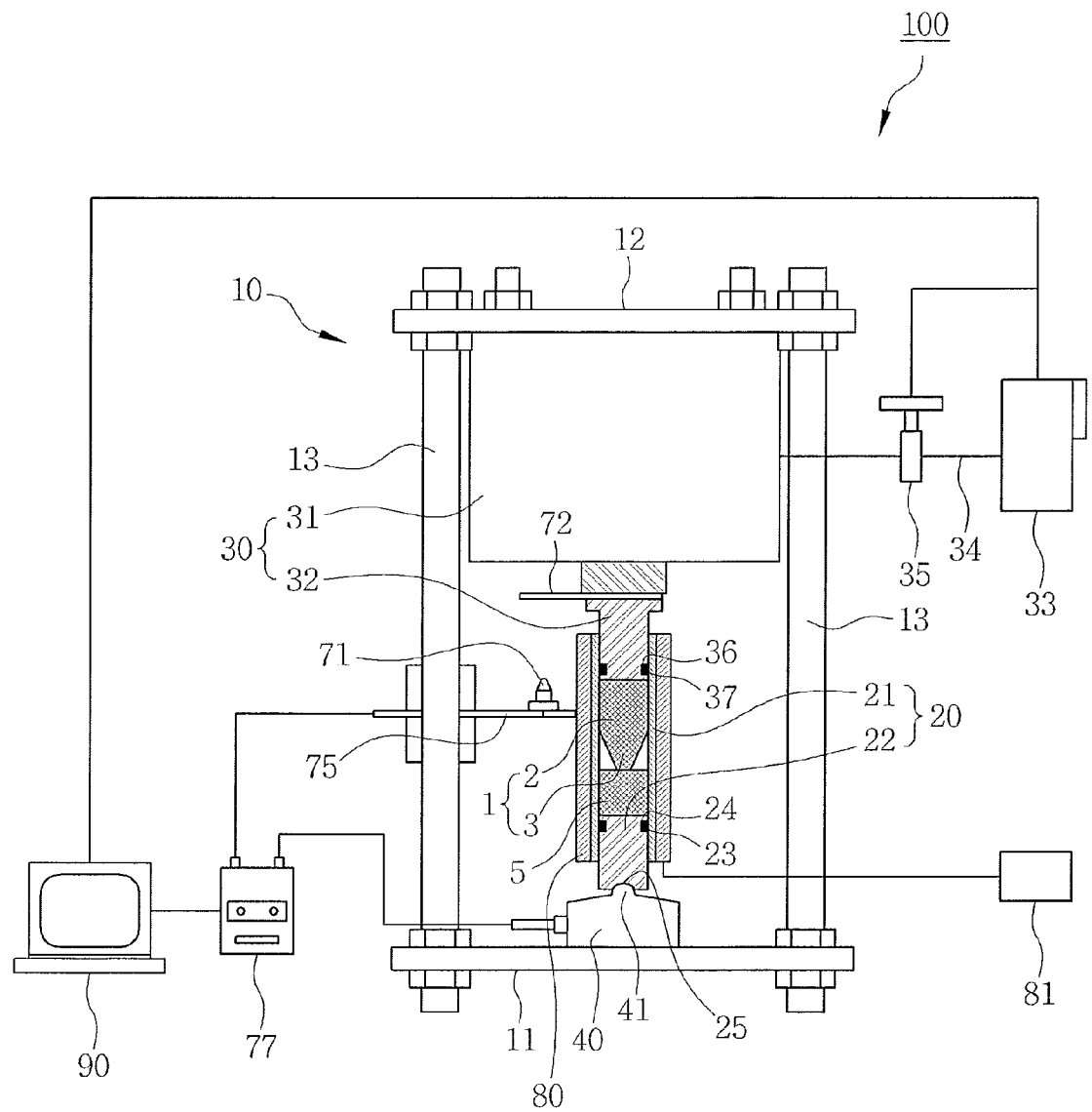
FIG. 1 is a schematic structural diagram of an apparatus for dissolution experiment of mineral according to an exemplary embodiment of the inventive concept.

Various example embodiments will be described more fully hereinafter with reference to the accompanying drawings, in which some example embodiments are shown. Inventive concepts may, however, be embodied in many different forms and should not be construed as limited to the example embodiments set forth herein. Rather, example embodiments are provided so that this disclosure will be thorough and complete, and will fully convey the scope of inventive concepts to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms. These terms are used to distinguish one element from another. Thus, a first element discussed below could be termed a second element without departing from the teachings of the inventive concepts. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
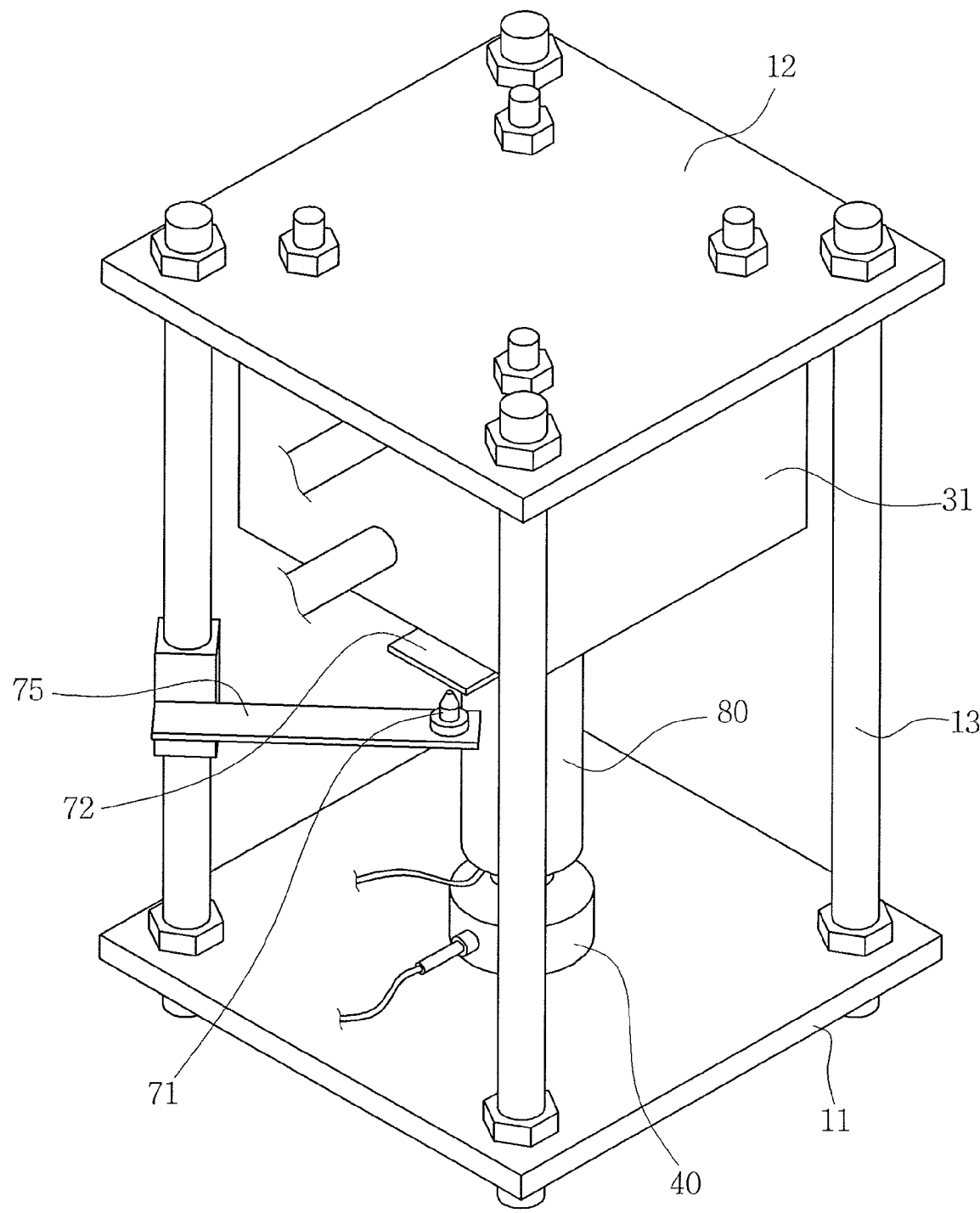
FIG. 2 is a schematic perspective view of the apparatus for dissolution experiment of mineral shown in FIG. 1.
Figure 3:
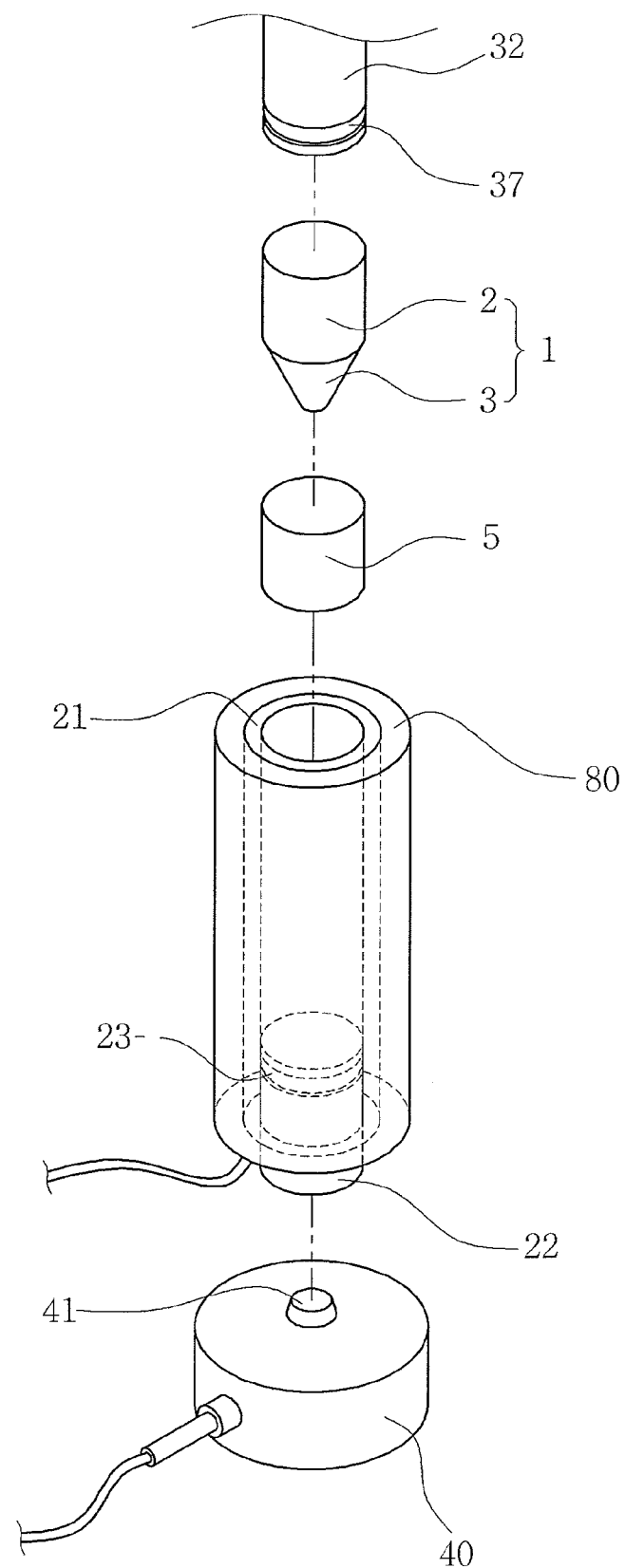
FIG. 3 is a schematic diagram for explaining mounting a first mineral sample and a second mineral sample in a mounting unit.

FIG. 1 is a schematic structural diagram of an apparatus for dissolution experiment of mineral according to an exemplary embodiment of the inventive concept, FIG. 2 is a schematic perspective view of the apparatus shown in FIG. 1, and FIG. 3 is a schematic diagram for explaining mounting a first mineral sample and a second mineral sample into a mounting unit. Referring to FIGS. 1 through 3, the apparatus for dissolution experiment of mineral (100) includes a main body (10), a mounting unit (20), a cylinder (30), and a load cell (40).

The main body (10) includes a flat base plate (11) and an upper plate (12) separated from the base plate (11) in an upper direction. The base plate (11) and the upper plate (12) are connected through four frames (13) vertically arranged.

The mounting unit (20) is for providing a mounting place of the first mineral sample and the second mineral sample used or the dissolution experiment and is composed of a tube (21) and a support (22).

The tube (21) is cylindrical and a hollow shape. The tube (21) of the inventive concept is made of polycarbonate. Polycarbonate has strong hardness enough to bear a pressure to be applied by a cylinder (30) and is transparent such that the inside may be visible to the naked eye.

The support (22) is inserted into the lower portion of the tube (21) and fixed. An O-ring (23) is interposed between the exterior surface of the support (22) and the inner surface of the tube (21) such that the support (22) may be barely inserted into the tube (21). In more detail, a fitting part (24) may be performed along the circumference of the exterior surface of the support (22), and the O-ring (23) contacts with the inner surface of the tube (21) with inserted into the fitting part (24). The gap between the support (22) and the tube (21) is sealed by the O-ring (23).

The mounting unit 20 is supported by the load cell (40). The load cell (40) to be described later is installed on the base plate (11) and includes a protrusion (41) on the upper surface, while the lower end surface of the support (21) having a concave groove (25) corresponding to the protrusion (41). The mounting unit (20) is supported by the load cell (40) with the protrusion (41) inserted into the groove (25).

A first mineral sample (1), a second mineral sample (5) and an alkaline solution (9) are contained in the mounting unit (20). The apparatus according to the inventive concept is for measuring dissolve behavior of mineral and may adopt various mineral as samples. An exemplary embodiment of the inventive concept uses quartz, single crystal mineral, a lot included in bentonite which is used for covering high level radioactive waste as a mineral sample.

The first mineral sample (1) and the second mineral sample (5) are both quartz, the second mineral sample (5) which is a cylinder shape is inserted into the tube (21) and supported on the supporter (22). And the first mineral sample (1) is inserted into the tube (21) so as to contact with the second mineral sample (5). The upper end portion (2) of the first mineral sample (1) is a cylinder shape, but the lower end portion has a sharp wedge part (3). The wedge part (3) has smaller diameters as proceeding from top to bottom gradually, and the bottom of the wedge part (3) contacts with the second mineral sample (5). The bottom of the wedge part (3) where the first mineral sample (1) and the second mineral sample contact has a diameter of about 1~3 mm.

As the lower end portion of the first mineral sample (1) is a wedge part (3), there generates a space around the wedge part (3) and the alkaline solution (9) is to be contained therein. That is, the first mineral sample (1) and the second mineral sample (5) contact with each other in the alkaline solution. As the lower portion of the mounting unit (20) is sealed with the O-ring (23), the alkaline solution (9) may not leak out.

Like the above, there are two reasons in forming the lower end portion of the first mineral sample (1) in a wedge shape.

The first reason is to adjust a pH term of the condition that the first mineral sample and the second mineral sample are set. That is, the solution for adjusting pH may be contained by preparing a space around the wedge part (3). The first mineral sample and the second mineral sample perform a function of covering radioactive waste buried under the ground and are to be exposed to the alkaline condition of underground depth of about 1 km. Thus, the wedge part (3) of the first mineral sample (1) and the upper face of the second mineral sample (5) need to be contained in the alkaline solution so as to form the contacting part of the first mineral sample and the second mineral sample as the alkaline condition.

The second reason is that the area of the contacting part needs to be small so as to form a high pressure with small force when pressing the first mineral sample and the second mineral sample to contact with each other by using the cylinder (30) in the experiment of dissolution behavior. Thus, the ending portion of the first mineral sample (1) is formed in a sharp form so as to form a high pressure with same force.

The cylinder (30) is for pressing the first mineral sample (1) and the second mineral sample (5) contacting with each other contained in the mounting unit (20). That is, the first mineral sample (1) and the second mineral sample (5) are under the condition of a high pressure in underground depth, thus, the cylinder (3) is prepared to give a pressure to the first mineral sample (1) and the second mineral sample (5) so as to form the same condition to the underground depth. In an exemplary embodiment, a pressure about maximum 20 MPa may be applied to the first mineral sample (1) and the second mineral sample (5).

A cylinder body (31) and a plunger (32) are included. The cylinder body (31) is combined to the rear surface of the upper plate (12) and fixed, and the plunger (32) may shift back and forth in the cylinder body (31).

The cylinder (30) uses air pressure, and the cylinder body (31) includes an airport (now shown) to which air is provided inside the cylinder body (31) by connecting air providing line (34) connected to an air pump (33). The plunger (32) shifts upward or downward according to the air production.

A regulator (35) is installed on the air providing line (34) between the cylinder body (31) and the air pump (33) to maintain the pressure applied by the plunger (32) constantly. If the condition changes, for example, the mineral sample is dissolved, after pressing has begun by the plunger (32), the pressure is changed, thus, the pressure from the plunger (32) needs to be maintained consistently through the regulator (35).

The plunger (32) is in a bar shape and has a bit smaller diameter than an internal diameter of the tube (21). Accordingly, the plunger (32) may be inserted inside the tube (21) when shifting downward. That is, when the plunger (32) shifts downward as air is provided into the cylinder body (31), the front end of the plunger (32) is inserted into the tube (21) and presses the first mineral sample (1). Inversely, the pressure is lifted when the plunger (32) shifts upward and leaves from the tube (21). And the front end of the plunger (32) has a groove (36) along the circumference where the O-ring (37) is to be inserted thereto so that the gap between the external surface of the plunger (32) and the internal surface of the tube (21) may be sealed when the plunger (32) is inserted into the mounting unit (20).

And, the displacement variation due to the dissolution of the first mineral sample (1) and the second mineral sample (5) at the first condition need to be measured in the dissolution experiment. In other words, usually the wedge part (3) dissolves (including dissolution of both the first mineral sample and the second mineral sample) when the first mineral sample (1) and the second mineral sample (5) contacts with each other by a pressure in an alkaline solution, at that time, the distance that the first mineral sample (1) shifted downward by the dissolution need to be measured.

The displacement of the plunger (32) may denote the displacement of the mineral samples due to the dissolution, as the experiment of the inventive concept is proceeded with a reference of the point where the plunger (32) contacts with the first mineral sample (1). The displacement sensor (70) is prepared for measuring the distance of the plunger (32) shifting.

In an exemplary embodiment, an eddy-current displacement transducer is used, wherein a sensor (71) is fixed to the frame (13) of the main unit (10) by a fixing bar (75), and a mover (72) that is mounted on the plunger (32). The mover (72) is in a bar shape, which is disposed horizontally and combined to the plunger (32), and an end portion thereof is disposed on the sensing path of the sensor (71). That is, the mover (72) is disposed above the sensor (71) and shifts up and down together with the plunger (32) shifting, such that the sensor (71) may sense the displacement variation of the plunger (32) by measuring the displacement variation of the mover (72).

The load cell (40) is for measuring the pressure applied to the mineral samples and supporting the mounting unit (20) as described above.

Meanwhile, according to an exemplary embodiment, a temperature controller is provided for reproducing the temperature condition of the underground depth where the first mineral sample (1) and the second mineral sample (2) are set. In an exemplary embodiment, a heat wire pad (80) is used for the temperature controller. The heat wire pad (80) wraps the tube (21) of the mounting unit (20). The heat wire pad (80) includes heat wires (not shown) generating heat by electric resistance, which is connected to a power source controller (81) electrically.

It is possible to perform the experiment under the same condition to the underground temperature by heating the first mineral sample (1) and the second mineral sample (5) by operating the heat wire pad (80). In an exemplary embodiment, it is possible to heat up about 50° C. centigrade.

The apparatus for dissolution experiment of mineral having the above composition enables to reproduce the underground condition of pressure, temperature and pH, accordingly, the dissolution behavior of quartz covering high-level radioactive waste in the underground condition may be exactly figured out.

A computer (90) for storing the condition of pressure, temperature, and pH, the pressure measured by the load cell under the condition, and the displacement variation measured by the displacement sensor is provided. The computer (90) is connected to each of a pressure-displacement recorder (77) which is connected to the load cell (40) and the displacement sensor (70), a power source controller of the heat wire pad (80), the air pump, and the regulator, electrically, stores and exchange data, and controls each of the devices.

Accordingly, a user may adjust pressure, temperature, or the like to fit the experiment condition through the computer, and the data is stored in real time, thereby enabling to figure out the dissolution behavior of mineral quantitatively.

As described above, the apparatus for dissolution experiment of mineral enables to reproduce the condition that mineral is set, that is, pressure, temperature, and pH, as it is, thus, it is possible to measure the dissolution behavior of mineral quantitatively.

As such, it is possible to maintain stability by checking the dissolution behavior of covering material, such as bentonite, according to the underground condition in advance, with reference to the quantitative experiment about dissolution behavior of mineral, when burying high-level radioactive waste.

While the present invention has been particularly shown and described with reference to exemplary embodiments thereof, it will be understood that various changes in form and details may be made therein without departing from the spirit and scope of the following claims.

What is claimed is:

1. An apparatus for a dissolution experiment of a mineral comprising:
   a main body;
   a mounting unit including a container whose upper portion is open so as to contain an alkaline solution, a first mineral sample and a second mineral sample contact with each other in the alkaline solution;
   a cylinder including a plunger that shifts so as to be inserted in or separated from the container for pressing the first mineral sample toward the second mineral sample mounted in the container of the mounting unit; and
   a load cell supporting the mounting unit from the below of the mounting unit and measuring the pressure applied to the second mineral sample,
   wherein the mounting unit is formed in a tube shape;
   the second mineral sample is inserted into the mounting unit;
   the first mineral sample is inserted into the mounting unit while forming a sharp wedge part such that the lower end portion of the wedge part contacts with the upper surface of the second mineral sample; and the alkaline solution is contained between the wedge part of the first mineral sample and the second mineral sample.

2. The apparatus for a dissolution experiment of a mineral of claim 1, wherein the apparatus further includes a temperature controller for adjusting the temperature of the first mineral sample and the second mineral sample contained in the mounting unit.

3. The apparatus for a dissolution experiment of a mineral of claim 2, wherein the temperature controller is a heat wire pad which wraps the exterior surface of the mounting unit and is composed of heat wires generating heat by electric resistance inside.

4. The apparatus for a dissolution of experiment of a mineral of claim 1, wherein the plunger further includes a regulator for maintaining a pressure applied to the first mineral sample constantly.

5. The apparatus for a dissolution experiment of a mineral of claim 1, wherein the apparatus further includes a displacement sensor for measuring the distance that the plunger shifts.

6. The apparatus for a dissolution experiment of a mineral of claim 5, wherein the displacement sensor including;

a sensor installed so as to be fixed to the main body; and a mover that is combined to the plunger and shifts along with the plunger, and an ending portion thereof is disposed on the sensing path of the sensor, wherein the displacement sensor measures the displacement variation of the plunger by sensing the distance from the sensor and the mover.

7. The apparatus for a dissolution experiment of a mineral of claim 1, wherein the contacting area of the first mineral sample and the second mineral sample is 1~3 mm in diameter.

8. The apparatus for a dissolution of experiment of a mineral of claim 1, wherein the mounting unit includes a cylindrical tube, a supporter inserted and fixed in the lower portion of the tube and supporting the second mineral sample, and an O-ring interposed between the exterior surface of the supporter and the inner surface of the tube and prevents the alkaline solution from being leaked out.

9. The apparatus for a dissolution experiment of a mineral of claim 8, wherein the lower end surface of the supporter includes a concave groove such that a protrusion formed on the upper surface of the load cell may be inserted thereto.

10. The apparatus for a dissolution experiment of a mineral of claim 8, wherein the tube of the mounting unit is composed of polycarbonate.

* * * * *